(12) United States Patent
McManus et al.

(10) Patent No.: US 6,380,401 B1
(45) Date of Patent: Apr. 30, 2002

(54) LACTONIZATION PROCESS

(75) Inventors: James McManus; Nicholas Anousis, both of Albany, GA (US); John Genus, Rock Hill, SC (US); Christopher Hancock, Augusta, GA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/694,190

(22) Filed: Oct. 23, 2000

Related U.S. Application Data

(60) Provisional application No. 60/161,876, filed on Oct. 27, 1999.

(51) Int. Cl.[7] ............................................ C07D 309/30
(52) U.S. Cl. ....................................... 549/292
(58) Field of Search ......................... 549/292

(56) References Cited

U.S. PATENT DOCUMENTS

| | | |
|---|---|---|
| 4,231,938 A | 11/1980 | Monagan et al. |
| 4,444,784 A | 4/1984 | Hoffman et al. |
| 4,582,915 A | 4/1986 | Steteinger et al. |
| 4,820,850 A | 4/1989 | Verhoeven et al. |
| 4,845,237 A | 7/1989 | DeCamp et al. |
| 4,916,239 A | 4/1990 | Treiber |
| 5,159,104 A | 10/1992 | Dabora et al. |
| 5,202,029 A | 4/1993 | Haytko et al. |
| 5,223,415 A | 6/1993 | Conder et al. |
| 5,250,435 A | 10/1993 | Cover et al. |
| 5,420,024 A | 5/1995 | Carta et al. |
| 5,650,523 A | 7/1997 | DeCamp et al. |
| 5,939,564 A | 8/1999 | Kumar et al. |

FOREIGN PATENT DOCUMENTS

| | | |
|---|---|---|
| EP | 351918 | 1/1990 |
| WO | WO1/00606 | 1/2001 |

OTHER PUBLICATIONS

Fukae, et al., Chem Abs. No. 27:134 (2001) [This is an English Language absttract of WO 01/00606].

*Primary Examiner*—Amelia Owens
(74) *Attorney, Agent, or Firm*—Carol S. Quagliato; Melvin Winokur

(57) ABSTRACT

Crystalline 3-hydroxylactone-containing products can be prepared in high yield and purity in a one-pot process by treating the corresponding 3,5-dihydroxy acid with a strong mineral acid in a cold, aprotic, water-miscible solvent to effect lactonization, followed by addition of excess acid to effect crystallization of the lactonized product from the reaction mixture.

63 Claims, No Drawings

LACTONIZATION PROCESS

RELATED APPLICATIONS

This application claims priority to U.S. Provisional Application No. 60/161,876, filed Oct. 27, 1999 which is hereby incorporated by reference in its entirety.

FIELD OF THE INVENTION

The present invention involves a lactonization process which is useful for making 3-hydroxy lactone-containing products, such as 3-hydroxy-3-methylglutaryl coenzyme A (HMG-CoA) reductase inhibitors.

BACKGROUND OF THE INVENTION

It has been clear for several decades that elevated blood cholesterol is a major risk factor for coronary heart disease (CHD), and many studies have shown that the risk of CHD events can be reduced by lipid-lowering therapy. Prior to 1987, the lipid-lowering arrnamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. With the introduction of lovastatin (MEVACOR®; see U.S. Pat. No. 4,231,938), the first inhibitor of HMG-CoA reductase to become available for prescription in 1987, for the first time physicians were able to obtain comparatively large reductions in plasma cholesterol with very few adverse effects.

In addition to the HMG-CoA reductase inhibitors which are natural fermentation products, mevastatin and lovastatin, there are now a variety of semi-synthetic and totally synthetic analogs thereof, including simvastatin (ZOCOR®; see U.S. Pat. No. 4,444,784), pravastatin (PRAVACHOL®; see U.S. Pat. No. 4,346,227), fluvastatin (LESCOL®; see U.S. Pat. No. 5,354,772), atorvastatin (LIPITOR®; see U.S. Pat. No. 5,273,995), cerivastatin (also known as rivastatin; see U.S. Pat. No. 5,177,080) and nisvastatin (also known as NK-104, see U.S. Pat. Nos. 5,284,953, 5,356,896 and 5,856,336). The hemi-calcium salt of nisvastatin is described and claimed in U.S. Pat. No. 5,856,336, while the structural formulas of the other noted HMG-CoA reductase inhibitors, as well as additional examples of HMG-CoA reductase inhibitors, are described at page 87 of M. Yalpani, "Cholesterol Lowering Drugs", Chemistry & Industry, pp. 85–89 (Feb. 5 1996). The HMG-CoA reductase inhibitors described above belong to a structural class of compounds which contain a moiety which can exist as either a 3-hydroxy lactone ring or as the corresponding open-ring 3,5-dihydroxy acid, as depicted below in the Scheme, and are commonly referred to as "statins."

The lactonized forms of the statins are metabolized to the active open-ring 3,5-dihydroxy acid form in the body. Lovastatin and simvastatin are marketed worldwide in their lactonized form. However, the preparation of the naturally occurring compounds and their semi-synthetic analogs leads to a mixture of the lactone and the open-ring 3,5-dihydroxy acid forms. Therefore, it is important to employ a high yielding and efficient method for lactonizing the open-ring form or a salt thereof.

Since lactonization is an equilibrium reaction, as illustrated in the Scheme below, some means of shifting the equilibrium to the "right," i.e., towards formation of the lactone, is required to achieve product in high yield and high purity.

SCHEME

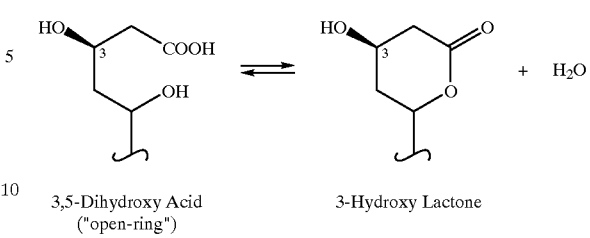

3,5-Dihydroxy Acid ("open-ring")      3-Hydroxy Lactone

In previous published procedures for making 3-hydroxy lactone-containing HMG-CoA reductase inhibitors, this equilibrium reaction was driven toward lactone formation by either (1) heating the dihydroxy acid in a neutral solvent with continuous removal of the water by-product, see U.S. Pat. No. 4,444,784, or by (2) removing the lactone product by adding water in order to crystallize out the lactone product, see U.S. Pat. No. 4,916,239.

When applying the technique of water removal to drive the equilibrium toward the desired lactone product, higher temperatures are required which promote an undesirable esterification reaction between the 3-hydroxy group of the 3-hydroxylactone with the precursor free acid to produce a dimeric impurity. As an example, the dimer of simvastatin is shown below. Reduction of the dimer impurity content in the final product is difficult, since standard purification methods such as re-crystallization, which requires heating, tend to promote further dimer formation.

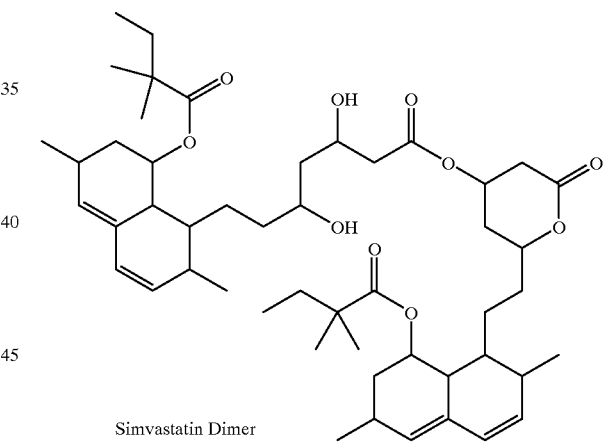

Simvastatin Dimer

Applying the approach of adding water to the reaction mixture to drive the equilibrium toward the lactone product mitigates the dimer impurity problem, but two other problems occur with this procedure. One problem is that the addition of water to effect crystallization of the product and drive the equilibrium toward the lactone side provides insufficient force to take the reaction to completion, resulting in contamination of the final product with unconverted starting material. This requires an additional purification step to produce a high purity product. A second problem is that when a water-miscible protic solvent such as acetic acid is used for the lactonization as is taught in U.S. Pat. No. 4,916,239, an esterification reaction between the solvent and the 3-hydroxy group of the 3-hydroxylactone occurs to produce 3-O-acylated lactone and corresponding 3-O-acylated open-ring 5-hydroxy acid side-product impurities which are not effectively removed, even after a subsequent purification step.

The instant invention provides a novel single-pot lactonization/purification process that can be used to produce 3-hydroxy lactone containing products, including statins, that avoids the aforementioned problems and provides a higher quality lactone product having a lower amount of total impurity than previously possible on a commercial scale. Particularly, all 3-O-acylated lactone and 3-O-acylated open-ring sideproduct impurities are eliminated. In addition, when the procedure is performed at sufficiently cold temperatures, the amount of dimer impurity in the final product measured by analytical HPLC as an area percentage is 0.1 area % or less. Therefore, the instant process eliminates the need for a separate purification step. The novel process described herein also results in a better yield and greater throughput in a single step.

SUMMARY OF THE INVENTION

One object of this invention is to provide an improved lactonization and purification process for making 3-hydroxy lactone-containing products in high yield using strong mineral acid to effect the lactonization and precipitation of the final product.

A second object is to employ the instant process for the preparation of 3-hydroxy lactone-containing HMG-CoA reductase inhibitors of the statin class.

A third object is to employ the process using a water-miscible, polar, 15 aprotic solvent thereby eliminating the formation of any 3-O-acylated lactone or 3-O-acylated open-ring side-product impurities.

A fourth object is to employ the process at sufficiently cold temperatures in order to decrease any dimer side-product impurity that forms to 0.20 area % or less, as quantified by analytical HPLC.

A fifth object is to employ the instant process under conditions so as to reduce the level of any single impurity that is present in the final product to 0.1 area % or less, as quantified by analytical HPLC.

A sixth object is to provide a process that can be adapted to be efficiently run on a large, factory scale.

A seventh object is to provide a commercial scale composition comprised of a 3-hydroxy lactone-containing product, for example a statin, and specific, reduced levels of chemical impurities that are present in the product.

Additional objects will be evident from the following detailed description.

DETAILED DESCRIPTION OF THE INVENTION

This invention is concerned with a novel process that can be performed in one pot for preparing a 3-hydroxy lactone-containing product from its corresponding open-ring 3,5-dihydroxy acid or a salt thereof.

The novel process for preparing a 3-hydroxy lactone-containing product from a salt of its corresponding open-ring 3,5-dihydroxy acid comprises the steps of:

(i) adding a strong mineral acid to a stirring suspension of the salt of a 3,5-dihydroxy acid-containing compound in a water-miscible organic solvent in an amount sufficient to protonate the salt and form the corresponding 3,5-dihydroxy acid;

(ii) adding additional strong mineral acid to the stirring solution of the 3,5-dihydroxy acid in an amount sufficient to lactonize the 3,5-dihydroxy acid to form a 3-hydroxy lactone-containing product;

(iii) adding an excess of additional strong mineral acid to the stirring reaction mixture in an amount sufficient to cause crystallization of the 3-hydroxy lactone-containing product;

(iv) collecting and washing the 3-hydroxy lactone-containing product; and (v) drying the washed 3-hydroxy lactone-containing product.

This one-pot process is illustrated in the Flow Sheet, below, wherein X is a salt-forming cation, and Y represents the chemical structural remainder of the 3,5-dihydroxy acid-containing compound and the 3-hydroxy lactone-containing product, as appropriate. Y can be any suitable chemical moiety that is amenable to the reaction conditions of the instant lactonization process.

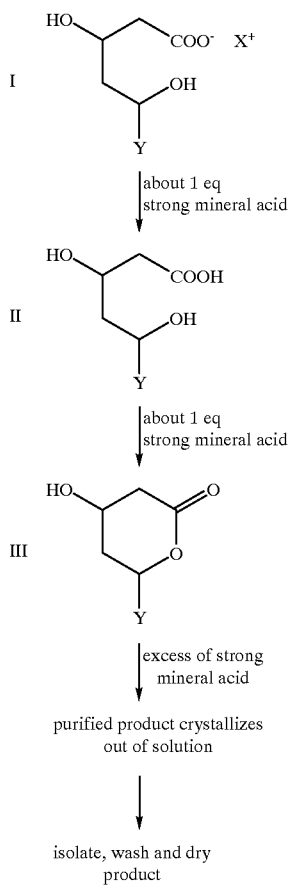

FLOW SHEET

The process of this invention has been described above as proceeding from salt (I) to acid (II) to lactone (III). Clearly, if the acid (II) is available for use as starting material, this invention includes, as one embodiment, the process of proceeding from acid (II) to lactone (III) and isolation of the lactone.

This process can be used to prepare, in one pot, highly purified 3-hydroxy lactone-containing compounds from the class of 3,5-dihydroxy acid-containing compounds or from salts thereof without the need for an additional purification procedure. In a second embodiment of this invention, the 3-hydroxy lactone-containing products are statins which have activity as HMG-CoA reductase inhibitors. One class of lactonized statins within this embodiment includes lovastatin and simvastatin. Additional members of this class include but are not limited to the lactonized forms of pravastatin, fluvastatin, atorvastatin, cerivastatin and nisvastatin.

An alternate class of compounds within this second embodiment includes 3,5-dihydroxy acids, or salts thereof, useful as starting materials and the corresponding lactonized products as defined by formulas I, II and III (see Flow Sheet) wherein Y is a member selected from the group consisting of

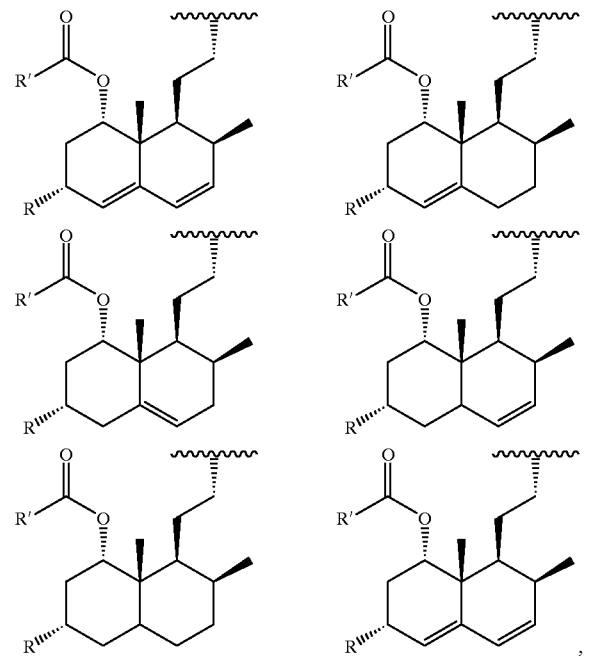

wherein R is selected from —OH and —CH$_3$; and R' is C$_{1-10}$ alkyl.

A sub-class of compounds within this alternate class are those wherein Y is a member selected from the group consisting of:

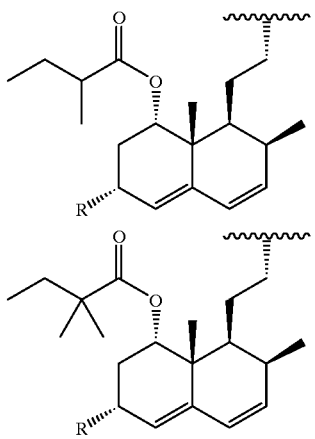

wherein R is selected from —OH and —CH$_3$.

A specific member of this sub-class is that wherein Y is

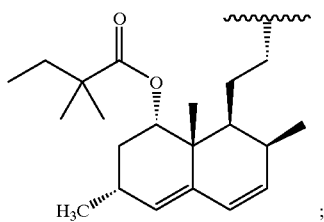

the lactonized form (formula III) of this specific member is simvastatin.

The starting material for the instant lactonization process is the desired lactone product's corresponding 3,5-dihydroxy acid or a salt thereof which is converted to the free acid prior to lactonization, as depicted in the Flow Sheet above, wherein X is any suitable salt-forming cation, including but not limited to those formed from such as sodium, potassium, aluminum, calcium, lithium, magnesium, zinc and tetramethylammonium, as well as from amines such as ammonia, ethylenediamine, N-methylglucamine, lysine, arginine, ornithine, β-choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane. A specific member of the class of salt forming cations is ammonium.

As used herein "alkyl" is intended to include both branched- and straight-chain saturated aliphatic hydrocarbon groups having the specified number of carbon atoms, e.g., methyl (Me), ethyl (Et), propyl (Bu), pentyl, hexyl, heptyl, octyl, nonyl, decyl and the isomers thereof such as isopropyl (i-Pr), isobutyl (i-Bu), secbutyl (s-Bu), tertbutyl (t-Bu), isopentyl, isohexyl and the like. The term "alkyl" includes both unsubstituted and substituted alkyl groups, for example mono-, di- and tri-substituted alkyl groups; one example is a benzyl group, wherein the aryl ring of the benzyl group may also be unsubstituted or substituted.

The term "dimer" or "dimeric impurity" as used herein is intended to include any esterification products that result from the reaction between the 3-hydroxy group of a 3-hydroxy lactone-containing compound and the free acid of a 3,5-dihydroxy acid-containing compound. Particularly, such dimers include the coupled statin dimers. Specific examples of compounds which are encompassed by the term dimer include, but are not limited to, the simvastatin dimer depicted above, and the analogous lovastatin dimer. The term dimer also includes the products formed by an esterification reaction between two different statins, for example the dimer product resulting from the reaction of the 3-OH group of simvastatin with 3,5-dihydroxy acid lovastatin (referred to herein as 3-O-mevinolinyl simvastatin), or alternately the reaction of the 3-OH group of lovastatin with 3,5-dihydroxy simvastatin. Analogous dimers resulting from other statins are readily envisioned and similarly encompassed.

The term "3-O-acylated impurities" as used herein is intended to include the side-product impurities formed by the esterification reaction between a carboxy-acid containing solvent and the 3-hydroxy group on the lactone or the 3-hydroxy group on the corresponding open-ring 3,5-dihydroxy acid, resulting in a 3-O-acyl group wherein the acyl group has the formula C$_{1-10}$—C(O)—. As used herein, the term "3-O-acylated impurities" does not include dimeric impurities. One example includes, but is not limited to, the 3-O-acylated sideproduct impurities derived from acetic acid, as depicted below,

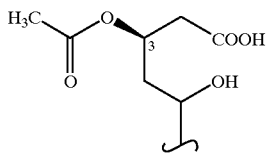
3-O-Acetyl 5-Hydroxy Acid ("open-ring")

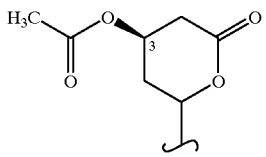
3-O-Acetyl Lactone and particularly may be 3-O-acetyl simvastatin and the corresponding 3-O-acetyl open-ring simvastatin.

The term "area %" as used herein is intended to be a unit of measurement for defining an indicated amount of a component compound contained in a composition. More specifically, the area % is the per cent composition determined by measuring the area of each peak and dividing the individual areas by the total area as determined by analytical HPLC, and particularly using the HPLC method defined in Example 4 herein. The formula for determining area % is represented as: area %=(area of component/total area of all components)×100.

The term "composition" as used herein is intended to be a solid chemical composition comprised of a 3-hydroxy lactone-containing product, for example a statin, and the chemical impurities that are present in the product. Impurities are intended to include undesired side-products formed in the reaction process. Examples of chemical impurities that may be present in the 3-hydroxy lactone-containing product include but are not limited to dimeric impurities (also referred to herein as dimer), and 3-O-acylated lactone and 3-O-acylated open-ring impurities. For example, certain impurities, which may be found in a simvastatin composition, depending on the process used to make the simvastatin, are listed in Example 4 herein.

The term "commercial scale composition" as used herein is intended to mean a commercial scale quantity of a composition which is produced as a single batch of at least 100 g of the composition. Embodiments of this invention include a commercial scale composition that is produced as a single batch of at least 100 g of the composition which has not been subjected to HPLC (high pressure liquid chromatography) purification, and a commercial scale composition that is produced as a single batch of at least 100 g of the composition which has not been subjected to any purification procedure. Examples include but are not limited to commercial scale compositions which are produced as a single batch of at least 100 g, at least 500 g, and at least one kilogram of the composition.

Another embodiment is a commercial scale composition comprised of a 3-hydroxy lactone-containing product absent 3-O-acylated impurities, and 0.20 area % or less of dimeric impurity. A particular example includes but is not limited to a commercial scale composition comprised of a 3-hydroxy lactone-containing product absent 3-O-acylated impurities, and 0.20 to 0.01 area % dimeric impurity.

Within this embodiment is a commercial scale composition comprised of a 3-hydroxy lactone-containing product absent 3-O-acylated impurities, and 0.1 area % or less of dimeric impurity. A particular example includes but is not limited to a commercial scale composition comprised of a 3-hydroxy lactone-containing product absent 3-O-acylated impurities, and 0.1 to 0.01 area % of dimeric impurity.

Also within this embodiment is a commercial scale composition comprised of a 3-hydroxy lactone-containing product absent 3-O-acylated impurities, 0.1 area % or less of dimeric impurity, and 0.1 area % or less of each of the other impurities present in the composition. A particular example includes but is not limited to a commercial scale composition comprised of a 3-hydroxy lactone-containing product absent 3-O-acylated impurities, 0.1 to 0.01 area % of dimeric impurity, and 0.1 to 0.01 area % of each of the other impurities present in the composition.

Further within this embodiment is a commercial scale composition comprised of a 3-hydroxy lactone-containing product absent 3-O-acylated impurities, 0.1 area % or less of dimeric impurity, 0.1 area % or less of 3-exomethylene simvastatin, and 0.10 area % or less of each of the other impurities present in the composition. A particular example includes but is not limited to a commercial scale composition comprised of a 3-hydroxy lactone-containing product absent 3-O-acylated impurities, 0.1 to 0.01 area % of dimeric impurity, 0.1 to 0.01 area % of 3-exomethylene simvastatin, and 0.10 to 0.01 area % of each of the other impurities present in the composition.

Also encompassed are any of the above-described commercial scale compositions comprised of 0.10 area % or less of dimeric impurity, for example but not limited to 0.10 to 0.01 area % of dimeric impurity. The phrase "absent 3-O-acylated impurities" as used herein includes for example 0.00 area % of 3-O-acylated impurities. Particularly, the 3-hydroxy lactone-containing product in the commercial scale composition is a statin, and even more particularly simvastatin. The 3-O-acyl group on the 3-O-acylated impurities may particularly be 3-O-acetyl.

The lactone product can be obtained using any suitable water-miscible aprotic or protic organic solvent. However, use of a protic solvent such as acetic acid or an alcohol leads to the problems of side-product formation from esterification reactions between the solvent and the 3-hydroxy group of the 3-hydroxylactone or the acid group of the dihydroxy acid precursor. An advantage of the claimed process is that all steps can be run in a water-miscible aprotic organic solvent, which completely avoids the formation of any 3-O-acylated side-product impurities. Members of the class of useful water-miscible aprotic solvents include but are not limited to acetonitrile, dimethylsulfoxide (DMSO), dimethyl formamide (DMF), tetrahydrofuran (THF), dioxane, and the like. A specific member of this class is acetonitrile.

The volume of aprotic solvent to be used should be at least sufficient to dissolve the 3,5-dihydroxy acid and lactone product, but not so great that inordinate volumes of strong mineral acid are required to cause crystallization of the lactone. Usually, volumes of about 4 L to about 6 L of aprotic solvent per kilogram of dihydroxy acid salt are appropriate.

Vigorous stirring of the reaction mixture during each addition of strong mineral acid should be maintained throughout the process. Sub-surface addition of strong mineral acid to the vigorously stirred reaction mixture is preferred. Vigorous stirring leads to larger crystal size and less occlusion of solvent and acid by the crystals.

The present process provides an advantage over previous lactonization processes in that the greater reactivity, lower lactone product solubility and greater freezing point depression provided by the use of strong rmineral acid to drive the equilibrium, allow the reaction to be run at low temperatures, thus limiting undesired side reactions. Although not necessary, it is preferable that the steps of the process, from the salt protonation step up to and including the collection and washing of the final product, be performed at a temperature of 10° C. or lower. One range of temperatures is from about 10° C. to about −15° C. A second range of temperatures is from about −8° C. to about −15° C. This novel process remains useful for making lactonized products if run at temperatures above 10° C.; however, the purity of the product will progressively suffer as the reaction temperature elevates, since the formation of a difficult to remove dimeric impurity increases as the temperature increases. As discussed above, the dimer is a side-product impurity that forms from an esterification reaction between the 3-hydroxyl group of the 3-hydroxy lactone product and the precursor free acid. It has been found that when practicing this process at reaction temperatures above about 10° C., the dimeric impurity begins to rise above about 0.2 area % in the final product, while at temperatures of 10° C. and lower, the dimeric impurity can be kept to about 0.2 area % or less in the final product. The most preferred temperature range of −8° C. to −15° C. provides the least amount of dimer formation, that is, 0.10 area % or less dimeric impurity in the final product.

Any strong mineral acid generally known to those of average skill in the art may be used with the present process. For optimum convenience and efficiency, it is desirable to use the same strong mineral acid for each of the protonation, lactonization and crystallization steps. However, the strong mineral acid need not be the same in each step in order to obtain the desired product. Examples of strong mineral acids that may be used include but are not limited to HCl, HBr, perfluoric acid, perchloric acid, phosphoric acid and nitric acid. An example of the class of strong mineral acids is HCl. As will be appreciated by those skilled in the art, the concentration of the strong mineral acid that can be used in the process of this invention can vary. For example, the concentration of strong mineral acid may efficently range from about 2N to about 6N, and illustratively about 4N, although other concentrations can be employed.

The amount of strong mineral acid useful in the process of this invention includes about 0.8 to 1.1 equivalents of strong mineral acid for each equivalent of 3,5-dihydroxy acid salt to effect protonation of the carboxylate salt, plus about 0.8 to about 1.1 equivalents additional strong mineral acid to effect ring closure. An excess of strong mineral acid is used to promote crystallization of the lactonized product from solution; an excess as used herein is intended to mean greater than one equivalent of mineral acid per equivalent of lactone product. More particularly, from about 2 to about 5 equivalents of strong mineral acid is useful to drive the reactive crystallization. Therefore, a total of about 4 to about 7 equivalents of acid may be used for the entire process. In addition, the reaction mixture may optionally be seeded at the crystallization step using standard techniques in the art to promote crystal formation.

Depending on the quality of the starting material it is sometimes appropriate to treat the solution of the 3,5-dihydroxy acid in solvent with decolorizing carbon followed by removal of the carbon before proceeding with the lactonization step. The temperature should be maintained within the cited ranges to assure the desired yield and purity.

The last steps of the process of this invention comprise the isolation (also referred to herein as collecting), washing and drying of the final product. Any means of separating solids from liquids can be employed for the isolation. However, for the scale exemplified herein it is convenient to pump the slurry of product and solvent into a centrifuge and follow it with washes. The washes can consist of a water miscible organic solvent described above or water or mixtures thereof, preferably at a temperature of 10° C. or lower as noted above. At this point, the washed product can be aged for an extended period of time at a temperature of about 15° C. to 20° C. However,. maximum yields and minimum amounts of 3,5-dihydroxy acid impurity are obtained if the final wash is about 0.1N to about 0.5N in strong mineral acid, particularly 0.1N and more particularly 0.1N HCl, followed by drying of the recovered material in a temperature range of about 35° C. to 50° C., and particularly at about 40° C.

In the Examples below, the following abbreviations are used:

| SAS | simvastatin ammonium salt |
| --- | --- |
| BHA | butylated hydroxyanisole |
| O/N | over night |
| MeCN | acetonitrile |
| MeOH | methanol |
| RT | room temperature |

EXAMPLE 1

Acetonitrile (40 mL) and butylated hydroxyanisole (BHA, 50 mg) were added to a 250 mL, 3-neck round bottom flask under a nitrogen atmosphere. The temperature was adjusted to −12° C. and simvastatin ammonium salt (10.34 g, 22.8 mmol) was then added, while maintaining good agitation. The ammonium salt was then protonated with one equivalent of cold (−12° C.) hydrochloric acid (4N, 5.7 mL) by adding the acid in subsurface manner at the tip of the impeller over 15 minutes, while maintaining the temperature at −12° C. The resulting solution was carbon treated (0.2 g), aged for three hours at −12° C. and filtered to remove the carbon and any extraneous matter that may be present. A second equivalent of HCl was then added, as above (−12° C., subsurface, 15 minutes). The reaction mixture was then seeded and the product crystallized over a five hour period by subsurface addition of HCl (4N, 60 mL), maintaining the above temperature. The product was isolated by filtration, washed with 1:1 methanol −0.1N HCl and dried under vacuum (50 mm Hg; 35° C.). Yield 97.3%; purity by HPLC 99.6%.

EXAMPLE 2

Acetonitrile (40 mL)and BHA (50 mg) were added to a 250 mL, 3-neck round bottom flask under a nitrogen atmosphere. The temperature was then adjusted to −12° C. and simvastatin ammonium salt (10.3 g, 22.8 mmol) was added, while maintaining good agitation, followed by addition of cold (−12° C.) hydrochloric acid (48%, 5 mL, 44.2 mmol) over 15 minutes, maintaining the temperature at −12° C. When dissolution was complete, hydrochloric acid (4N, 30 mL) was added in one portion. the reaction mixture was then seeded with pure simvastatin (50 mg) and the pure simvastatin product crystallized by subsurface addition of hydrochloric acid (4N, 12 hours). The product was filtered, washed with cold (−12° C.) 1:1 methanol/0.1lN HCl, and vacuum dried (50 mm Hg; 30–35° C., 12 hours). Yield 97.1%; Purity by HPLC 99.5%.

EXAMPLE 3

Acetonitrile (4 L) and BHA (5 g) were added to a 16-liter, full-jacket, cylindrical, glass reactor under a nitrogen atmosphere and the solution cooled to −13° C. Simvastatin ammonium salt (1000 g, 2.2 mol) was then added while maintaining good mixing using an agitator containing two 45° pitched-four-bladed turbines (diameter 4.5 inches) set at an agitation rate of 250 rpm. The ammonium salt was then protonated by adding 500 mL cold (−13° C.) 4N HCl in one shot. Additional cold 4N HCl (3.5 L) was then added subsurface over an eight hour period; the reaction mixture was seeded with pure simvastatin (20 g) after having added 1.5 L of the acid. Additional 4N HCL (4 L) was next added in the same manner over a four hour period. Following the crystallization with this last acid addition, the reaction mixture was aged at −15° C. for one hour. The product was isolated by centrifugation, washed with 1 L of 30% aqueous acetonitrile at RT, followed by 2 L of 1:1 MeOH $H_2O$ adjusted to 0.1N in HCl at −10° C., then dried in a rotary vacuum dryer for 7 hours at 45° C. and 25 mm Hg pressure. Yield 98%; purity by HPLC 99.6%.

In the foregoing Examples, the lactonization yields were typically 98% and the purities equal to or greater than 99.6% with no single impurity greater than 0.1%. These purity values are better than those generated with the prior process of adding water to the reaction mixture in order to crystallize out the lactone product.

EXAMPLE 4

I. Analytical Method—HPLC (High Performance Liquid Chromatography)

A. Reagents

1. Water
2. Acetonitrile (ACN)
3. Phosphoric Acid ($H_3PO_4$)
4. Potassium Phosphate Monobasic ($KH_2PO_4$)
5. Simvastatin Reference Standard B. Solutions 1. Mobile Phase A—Add 1.0 mL of $H_3PO_4$ into a 1 L volumetric flask containing about 300 mL of water. Dilute to volume with water and mix. Mix this solution with 1 L of acetonitrile and filter/degas prior to use.
2. Mobile Phase B—Add 1.0 mL of $H_3PO_4$ into a 1 L volumetric flask containing about 300 mL of acetonitrile. Dilute to volume with acetonitrile and mix.
3. Diluent—Dissolve 0.055 g of $KH_2PO_4$ in 400 mL of water. Adjust the pH to 4.0 with phosphoric acid. Mix this solution with 600 mL of acetonitrile and filter prior to use.

C. Chromatographic Conditions

To minimize system dead volume, all connections from the auto sampler to the column and the column to the detector should be with 0.007 inch I.D. tubing, with no single piece longer than 10 cm.

Column: Perkin-Elmer Pecosphere cartridge, C18 CR. 33 mm ×4.6 I.D., 3μm particles inserted in a 3.3 cm cartridge holder.

Flow Rate: 3.0 mL/minute

Temperature: Ambient

Detection: 200 nm & 238 nm

Injection Vol.: 25 μL & 5 μL

Run Time: 13 minutes

| Gradient: | | |
|---|---|---|
| Time (min) | % A | % B |
| 0.0 | 100 | 0 |
| 4.5 | 100 | 0 |
| 4.6 | 95 | 5 |
| 8.0 | 25 | 75 |
| 11.5 | 25 | 75 |
| 11.6 | 100 | 0 |
| 13.0 | 100 | 0 |

II. Using the Analytical HPLC Method Described Above, the Following Relative Retention Times were Observed to be Associated with the Listed Simvastatin Impurities.

| Impurity | Relative Retention Time (RRT) |
|---|---|
| 5-Hydroxyacid Simvastatin (Open-ring Simvastatin) | 0.447 |
| Lovastatin | 0.635 |
| 3-Exomethylene Simvastatin | 0.810 |
| Simvastatin Methyl Ester | 1.100 |
| Dihydrosimvastatin | 1.260 |
| 3-0-Acetyl Simvastatin | 2.590 |
| Dehydrosimvastatin | 2.669 |
| 3-0-Mevinolinyl Simvastatin | 3.945 |
| Simvastatin Dimer | 4.455 |

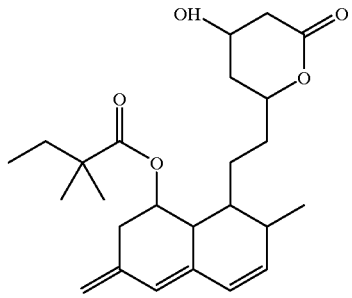

3-Exomethylene Simvastatin
(RRT 0.810)

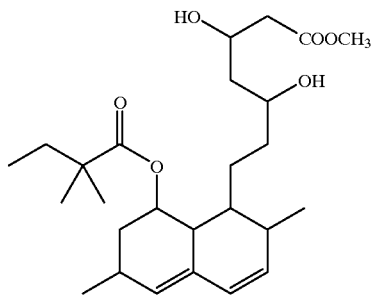

Simvastatin Methyl Ester
(RRT 1.100)

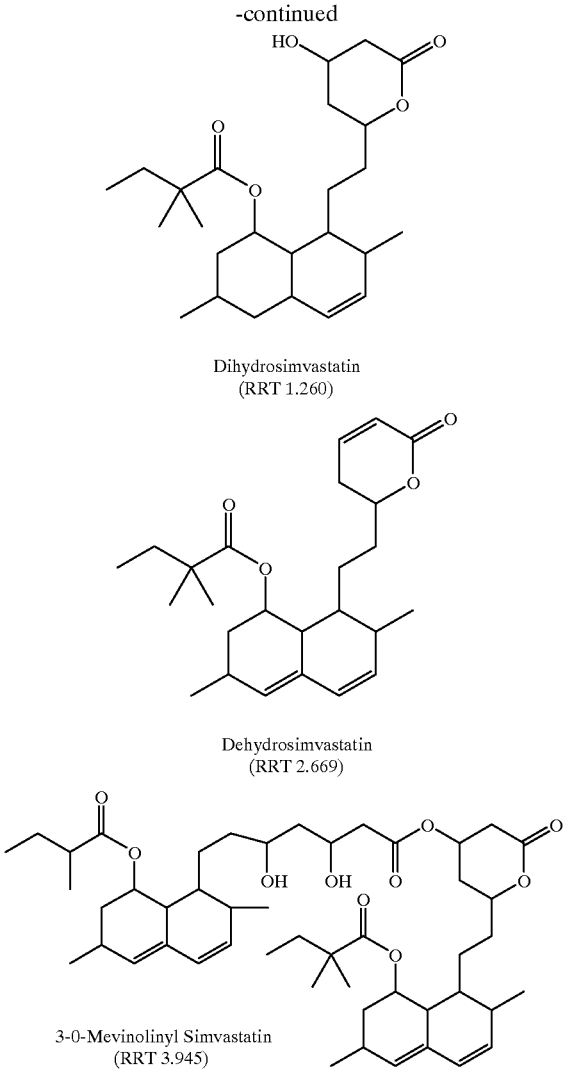

Dihydrosimvastatin
(RRT 1.260)

Dehydrosimvastatin
(RRT 2.669)

3-O-Mevinolinyl Simvastatin
(RRT 3.945)

While the invention has been described and illustrated with reference to certain particular embodiments thereof, those skilled in the art will appreciate that various changes, modifications and substitutions can be made therein without departing from the spirit and scope of the invention. It is intended, therefore, that the invention be defined by the scope of the claims which follow and that such claims be interpreted as broadly as is reasonable.

What is claimed is:

1. A process for preparing a 3-hydroxy lactone-containing product from its corresponding open-ring 3,5-dihydroxy acid comprising the steps of:
   (i) adding a strong mineral acid to a stirring solution of the 3,5-dihydroxy acid in a water-miscible organic solvent, in an amount sufficient to lactonize the 3,5-dihydroxy acid to form the 3-hydroxy lactone-containing product;
   (ii) adding an excess of additional strong mineral acid to the stirring reaction mixture in an amount sufficient to cause crystallization of the 3-hydroxy lactone-containing product;
   (iii) collecting and washing the 3-hydroxy lactone-containing product; and
   (iv) drying the washed 3-hydroxy lactone-containing product.

2. The process of claim 1 wherein the water-miscible organic solvent is an aprotic solvent.

3. The process of claim 2 wherein the water-miscible organic solvent is an aprotic solvent selected from the group consisting of acetonitrile, dimethylsulfoxide, dimethyl formamide, tetrahydrofuran and dioxane.

4. The process of claim 3 wherein the water-miscible organic solvent is acetonitrile.

5. The process of claim 1 wherein the strong mineral acid used in steps (i) and (ii) is the same.

6. The process of claim 1 wherein the strong mineral acid is selected from the group consisting of hydrochloric acid, hydrobromic acid, perfluoric acid, perchloric acid, phosphoric acid and nitric acid.

7. The process of claim 6 wherein the strong mineral acid is hydrochloric acid.

8. The process of claim 7 wherein the strong mineral acid is 4N hydrochloric acid.

9. The process of claim 1 wherein from about 0.8 to 1.1 equivalents of strong mineral acid per each equivalent of open-ring 3,5-dihydroxy acid is used to effect lactonization of the 3,5-dihydroxy acid.

10. The process of claim 1 wherein from about 2 to 5 equivalents of strong mineral acid per each equivalent of 3-hydroxy lactone-containing product is used to cause crystallization of the lactone-containing product.

11. The process of claim 1 wherein steps (i), (ii) and (iii) are performed at a temperature of 10° C. or lower.

12. The process of claim 1 wherein steps (i), (ii) and (iii) are performed at a temperature in the range from 10° C. to −15° C.

13. The process of claim 1 wherein steps (i), (ii) and (iii) are performed at a temperature in the range from −8° C. to −15° C.

14. The process of claim 1 wherein the 3,5-dihydroxy acid is treated with decolorizing carbon followed by removal of the decolorizing carbon before proceeding to step (i).

15. The process of claim 1 wherein the reaction mixture containing the 3-hydroxy lactone-containing product is seeded in order to promote crystal formation.

16. The process of claim 1 wherein the solvent used for the final wash of the collected product in step (iii) is comprised of about 0.1N to 0.5N strong mineral acid.

17. The process of claim 1 wherein the 3-hydroxy lactone-containing product is a statin in its lactone form.

18. The process of claim 17 wherein the statin has the structural formula III

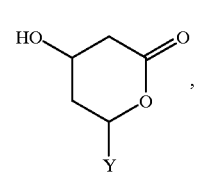

III wherein Y is a member selected from the group consisting of:

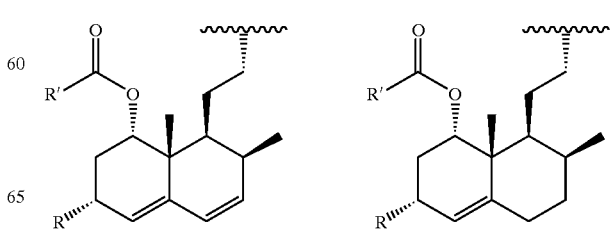

-continued

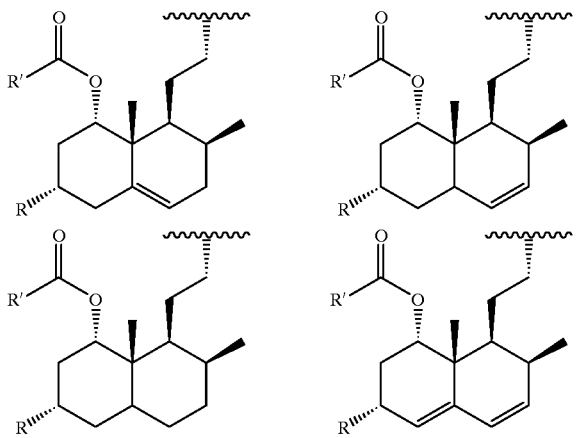

and wherein R is selected from —OH and —CH$_3$; and R' is C$_{1-10}$ alkyl.

19. The process of claim 17 wherein the 3-hydroxy lactone-containing product is simvastatin.

20. The process of claim 17 wherein the 3-hydroxy lactone-containing product is lovastatin.

21. The process of claim 17 wherein the 3-hydroxy lactone-containing product is the lactonized form of a statin selected from the group consisting of pravastatin, fluvastatin, atorvastatin, cerivastatin, and nisvastatin.

22. The process of claim 1 for preparing a 3-hydroxy lactone-containing statin from its corresponding open-ring 3,5-dihydroxy acid comprising the steps of:
(i) adding 0.8 to 1.1 equivalents of strong mineral acid per equivalent of the 3,5-dihydroxy acid to a stirring solution of the 3,5-dihydroxy acid in an aprotic organic solvent to cause lactonization;
(ii) adding an excess of additional strong mineral acid to the stirring reaction mixture in an amount sufficient to cause crystallization of the 3-hydroxy lactone-containing product;
(iii) collecting and washing the 3-hydroxy lactone-containing product; and
(iv) drying the washed 3-hydroxy lactone-containing product;
wherein steps (i), (ii) and (iii) areperformed at a temperature of 10° C. or lower.

23. The process of claim 22 wherein steps (i), (ii) and (iii) are performed at a temperature in the range from −8° C. to −15° C.

24. The process of claim 23 wherein statin is selected from lovastatin and simvastatin.

25. The process of claim 24 wherein the aprotic solvent is acetonitrile and the strong mineral acid is hydrochloric acid.

26. The process of claim 25 wherein the 3-hydroxy lactone-containing product is simvastatin.

27. The process of claim 26 wherein from about 2 to 5 equivalents of strong mineral acid per each equivalent of simvastatin is used to cause crystallization in step (ii).

28. The process of claim 27 wherein the solvent used for the final wash of the collected product in step (iii) is comprised of about 0.1N to 0.5N hydrochloric acid.

29. The process of claim 28 wherein the washed 3-hydroxy lactone-containing product is dried at a temperature in the range from 35° C. to 50° C.

30. The process of claim 1 further comprising an initial step of forming the 3,5-dihydroxy acid by treating a salt of the 3,5-dihydroxy acid in a water-miscible organic solvent with a strong mineral acid in an amount sufficient to protonate the salt and form the corresponding 3,5-dihydroxy acid.

31. The process of claim 30 wherein the protonation, lactonization and crystallization steps are performed in a single reaction pot.

32. The process of claim 30 wherein the water-miscible organic solvent is an aprotic solvent.

33. The process of claim 32 wherein the water-miscible organic solvent is an aprotic solvent selected from the group consisting of acetonitrile, dimethylsulfoxide, dimethyl formamide, tetrahydrofuran and dioxane.

34. The process of claim 33 wherein the water-miscible organic solvent is acetonitrile.

35. The process of claim 30 wherein the same strong mineral acid is used throughout the process.

36. The process of claim 30 wherein the strong mineral acid is selected from the group consisting of hydrochloric acid, hydrobromic acid, perfluoric acid, perchloric acid, phosphoric acid and nitric acid.

37. The process of claim 36 wherein the strong mineral acid is hydrochloric acid.

38. The process of claim 37 wherein the strong mineral acid is 4N hydrochloric acid.

39. The process of claim 30 wherein from about 0.8 to 1.1 equivalents of strong mineral acid per each equivalent of open-ring 3,5-dihydroxy acid salt is used to protonate the salt and form the corresponding 3,5-dihydroxy acid.

40. The process of claim 30 wherein from about 0.8 to 1.1 equivalents of strong mineral acid per each equivalent of open-ring 3,5-dihydroxy acid is used to effect lactonization of the 3,5-dihydroxy acid.

41. The process of claim 30 wherein from about 2 to 5 equivalents of strong mineral acid per each equivalent of 3-hydroxy lactone-containing product is used to cause crystallization of the lactone-containing product.

42. The process of claim 30 wherein the initial protonation step and the subsequent steps (i), (ii) and (iii) are performed at a temperature of 10° C. or lower.

43. The process of claim 30 wherein the initial protonation step and the subsequent steps (i), (ii) and (iii) are performed at a temperature in the range from 10° C. to −15° C.

44. The process of claim 30 wherein the initial protonation step and the subsequent steps (i), (ii) and (iii) are performed at a temperature in the range from −8° C. to −15° C.

45. The process of claim 30 wherein the 3,5-dihydroxy acid is treated with decolorizing carbon followed by removal of the decolorizing carbon before proceeding to step (i).

46. The process of claim 30 wherein the reaction mixture containing the 3-hydroxy lactone-containing product is seeded in order to promote crystal formation.

47. The process of claim 30 wherein the solvent used for the final wash of the collected product is comprised of about 0.1N to 0.5N strong mineral acid.

48. The process of claim 30 wherein the 3-hydroxy lactone-containing product is a statin in its lactone form.

49. The process of claim 48 wherein the statin has the structural formula III

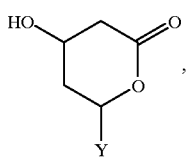

wherein Y is a member selected from the group consisting of:

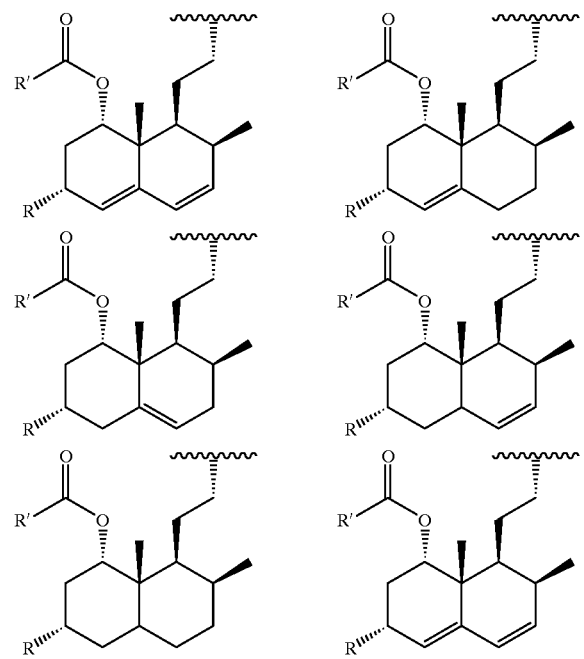

and wherein R is selected from —OH and —CH$_3$; and R' is C$_{1-10}$ alkyl.

50. The process of claim 48 wherein the 3-hydroxy lactone-containing product is simvastatin.

51. The process of claim 48 wherein the 3-hydroxy lactone-containing product is lovastatin.

52. The process of claim 48 wherein the 3-hydroxy lactone-containing product is the lactonized form of a statin selected from the group consisting of pravastatin, fluvastatin, atorvastatin, cerivastatin, and nisvastatin.

53. A process for preparing a 3-hydroxy lactone-containing statin from a salt of its corresponding open-ring 3,5-dihydroxy acid comprising the steps of:
(i) adding 0.8 to 1.1 equivalents of strong mineral acid per equivalent of 3,5-dihydroxy acid salt to a stirring mixture of the 3,5-dihydroxy acid salt in an aprotic organic solvent to protonate the salt and form the corresponding 3,5-dihydroxy acid;
(ii) adding 0.8 to 1.1 equivalents of strong mineral acid per equivalent of 3,5-dihydroxy acid to the stirring reaction mixture to cause lactonization;
(iii) adding an excess of additional strong mineral acid to the stirring reaction mixture in an amount sufficient to cause crystallization of the 3-hydroxy lactone-containing product;
(iv) collecting and washing the 3-hydroxy lactone-containing product; and
(v) drying the washed 3-hydroxy lactone-containing product;
wherein steps (i), (ii), (iii) and (iv) are performed at a temperature of 10° C. or lower.

54. The process of claim 53 wherein steps (i), (ii), (iii) and (iv) are performed at a temperature in the range from −8° C. to −15° C.

55. The process of claim 54 wherein the statin is selected from lovastatin and simvastatin.

56. The process of claim 55 wherein the salt of the statin is the ammonium salt.

57. The process of claim 55 wherein the aprotic solvent is acetonitrile and the strong mineral acid is hydrochloric acid.

58. The process of claim 57 wherein the 3-hydroxy lactone-containing product is simvastatin.

59. The process of claim 58 wherein from about 2 to 5 equivalents of strong mineral acid per each equivalent of simvastatin is used to cause crystallization in step (iii).

60. The process of claim 59 wherein the solvent used for the final wash of the collected product in step (iv) is comprised of about 0.1N to 0.5N hydrochloric acid.

61. The process of claim 60 wherein the washed 3-hydroxy lactone-containing product is dried at a temperature in the range from 35° C. to 50° C. in step (v).

62. The process of claim 53 wherein the 3,5-dihydroxy acid is treated with decolorizing carbon followed by removal of the decolorizing carbon before the lactonization step.

63. The process of claim 53 wherein the reaction mixture containing the 3-hydroxy lactone-containing product in step (iii) is seeded in order to promote crystal formation.

* * * * *